(12) United States Patent
De Cola et al.

(10) Patent No.: US 8,440,826 B2
(45) Date of Patent: May 14, 2013

(54) LIGHT EMITTING CU (I) COMPLEXES

(75) Inventors: Luisa De Cola, Münster (DE); Yinghui Sun, The Floravale (SG); Franz Schwarzenbach, Frenkendorf (CH); Doris Schwarzenbach, legal representative, Frenkendorf (CH); Oliver Schwarzenbach, legal representative, Frenkendorf (CH); Stefanie Schwarzenbach, legal representative, Frenkendorf (CH); Roger Prétôt, Basel (CH)

(73) Assignee: BASF SE, Ludwigshafen (DE)

( * ) Notice: Subject to any disclaimer, the term of this patent is extended or adjusted under 35 U.S.C. 154(b) by 414 days.

(21) Appl. No.: 12/663,769

(22) PCT Filed: Jun. 13, 2008
(Under 37 CFR 1.47)

(86) PCT No.: PCT/EP2008/057453
§ 371 (c)(1),
(2), (4) Date: May 18, 2010

(87) PCT Pub. No.: WO2009/000673
PCT Pub. Date: Dec. 31, 2008

(65) Prior Publication Data
US 2010/0252820 A1    Oct. 7, 2010

(30) Foreign Application Priority Data

Jun. 22, 2007  (EP) .................. 07110872.4

(51) Int. Cl.
*C07F 1/08* (2006.01)
*H01L 51/50* (2006.01)
(52) U.S. Cl.
USPC .............................. 546/2; 313/504; 428/690
(58) Field of Classification Search ....... 546/2; 313/504; 428/690
See application file for complete search history.

(56) References Cited

U.S. PATENT DOCUMENTS

| | | |
|---|---|---|
| 2005/0014024 A1 | 1/2005 | Tsuboyama et al. |
| 2005/0221115 A1 | 10/2005 | Tsuboyama et al. |
| 2006/0286404 A1 | 12/2006 | Wu |
| 2007/0267959 A1 | 11/2007 | Ragini et al. |
| 2008/0015355 A1 | 1/2008 | Schafer et al. |
| 2009/0062560 A1 | 3/2009 | Pretot et al. |
| 2010/0044688 A1 | 2/2010 | Wolleb et al. |
| 2010/0108994 A1 | 5/2010 | Schafer et al. |
| 2011/0114922 A1 | 5/2011 | Pretot et al. |

FOREIGN PATENT DOCUMENTS

| | | |
|---|---|---|
| JP | 2008-303152 A | 12/2008 |
| WO | 03/095587 A1 | 11/2003 |
| WO | 20071028417 A1 | 3/2007 |

OTHER PUBLICATIONS

Zhang, J-P. et al.: Copper(I) 1,2,4-triazolates and related complexes. J. Am. Chem. Soc. vol. 127, pp. 5495-5506, 2005.*
Badiei et al., J. Am. Chem. Soc. vol. 128, (Nov. 2006) pp. 15056-15057.
Brown et al., Inorganic Chemistry, vol. 46, No. 2, (Jan. 2007) pp. 486-496.
York et al., Inorganic Chemistry, vol. 45, No. 10, (May 2006) pp. 4191-4198.
Badiei et al. Journal of organometallic chemistry, vol. 690, No. 24-25, (Dec. 2005) pp. 5989-6000.
Blue et al., Journal of the American Chemical Society, vol. 125, No. 31, (Aug. 2003) pp. 9435-9441.
Goj et al., Inorganic Chemistry, vol. 45, No. 22, (Oct. 2006) pp. 9032-9045.
T. Yamamoto, Bull. Chem. Soc. Jpn, vol. 53, (Jan. 1980) pp. 1299-1302.
English language abstract No. 2009-A58232/03 of JP 2008-303152.
Y. Inoue et al., Macromolecules 2003, 36, pp. 7432-7438.
R. Rader et al., J. Am. Chem. Soc. 1981, 103, pp. 5906-5912.
V.Beck et al., Inorg. Nucl. Chem. Letters vol. 4, pp. 143-146 (1968).
P.G. Rasmussen et al., Inorganica Chimica Acta, 118 (1986) pp. 7-13.
S. de Souza Lemos et al., Z. anorg. allg. Chem. 624 (1998) pp. 701-707.
G. Attilio Ardizzoia et al., Inorganica Chimica Acta, 158 (1989) pp. 159-165.
Yinghui Sun: Curriculum Vitae, [Online] Jun. 24, 2007,—Jun. 28, 2007 XP002495606.

* cited by examiner

*Primary Examiner* — Charanjit Aulakh
(74) *Attorney, Agent, or Firm* — Shiela A. Loggins

(57) ABSTRACT

Electroneutral metal complexes of the formula I

L Cu A    (I)

wherein
L stands for an, especially bidentate, neutral ligand and
A stands for an, especially bidentate, monoanionic ligand binding to Cu by at least one heteroatom selected from N, P, S;
or wherein the ligands L and A with the above features are interconnected by at least one chemical bond to form one common tetradentate ligand;
or protonated or alkylated forms or salts thereof
show good light emitting efficiency in electroluminescent applications.

7 Claims, 8 Drawing Sheets

LIGHT EMITTING CU (I) COMPLEXES

This invention concerns with the design and characterization of neutral complexes of Cu(I) metal ion, its application inter alia in light emitting electronic devices, especially of blue and green emission, with corresponding uses and processes, and with some novel ligands useful for the preparation of the present complexes.

A number of electroluminiscent Cu(I) complexes have been described by Rader et al. (J. Am. Chem. Soc. 103, 5906 (1981)) and Tsuboyama et al. (US-2005/014024; WO 03/095587). Certain mononuclear electroneutral copper complexes have been proposed mainly as catalysts, see, for example, Inoue et al., Macromolecules 36, 7432 (2003).

A new group of electroneutral Cu(I) complexes now has been found which has especially valuable properties for light emitting devices such as OLED (organic light emitting diodes) or LEC (light emitting cells), for example with respect to the spectral emission characteristics, and good solubility in many solvents including THF, Toluene, dichloromethane. Further advantages of devices containing the present compounds include easy handling, disposability and low toxicity, and high lifetime/low sensitivity against oxidants.

The present invention thus pertains to an electroneutral complex of the formula I

$$L\ Cu\ A \qquad (I)$$

wherein
L stands for a neutral ligand and
A stands for a monoanionic ligand binding to Cu by at least one heteroatom selected from N, P, S;
or wherein the ligands L and A with the above features are interconnected by at least one chemical bond to form one common tetradentate ligand
or a protonated or alkylated form or salt thereof.

A usually is a heterocyclic ligand containing the bonding heteroatom, especially nitrogen and/or sulphur, as a ring atom. Examples for such heterocyclics ($C_1$-$C_{18}$, which optionally may be substituted) are listed further below.

The complex of the formula I usually is a tetracoordinated complex, e.g. wherein both L and A are bidentate ligands, L is a tridentate ligand and A is a monodentate ligand, L is a monodentate ligand and A is a tridentate ligand, or L and A with the above features are interconnected by at least one chemical bond to form one common tetradentate ligand.

The present compounds, especially those wherein a heteroatom in ligand A is nitrogen, further may be used for sensoring purposes, e.g. due to the finding that a significant shift in the emission colour may be achieved by modification of the ligand, e.g. protonation or alkylation such as methylation, especially at the nitrogen atom. In consequence, such complexes are no longer electroneutral but carry, in consequence of the adduction of the modifier such as H+ or $CH_3$+, a positive charge. Thus modified complexes may therefore be described as adduction salts (such as hydrohalides, hydrosulfates, methylsulfates or methylhalides) of the primary electroneutral complex.

In a class of primary technical interest of complexes of the formula I,
L stands for a bidentate neutral ligand and
A stands for a bidentate monoanionic ligand binding to Cu by at least one heteroatom selected from N, P, S;
or wherein the ligands L and A with the above features are interconnected by at least one chemical bond to form one common tetradentate ligand
or a protonated or methylated form or salt thereof.

In preferred ligands A, the negative charge is located mainly at the heteroatom mentioned.

In general, the compounds present a tetrahedral geometry. They are especially stable towards dioxygen and solvents.

The present complexes are weakly emitting in oxygenated solution, but become strongly luminescent in the solid or if mixed with a polymer such as PMMA or PVK.

As noted above, the 2 ligands A and L may be interlinked by bridging groups or one or more chemical bonds to form one chemical entity (one common tetradentate ligand). The interlinkage is formally achieved by replacement of at least one H atom on each of the ligands by a chemical bond.

A preferred group of complexes contain one ligand based on a bisPhosphine derivative and one negatively charged N—N ligand.

Alkyl stands for any acyclic saturated monovalent hydrocarbyl group; alkenyl denotes such a group but containing at least one carbon-carbon double bond (such as in allyl); similarly, alkynyl denotes such a group but containing at least one carbon-carbon triple bond (such as in propargyl). In case that an alkenyl or alkynyl group contains more than one double bond, these bonds usually are not cumulated, but may be arranged in an alternating order, such as in —[CH=CH—]$_n$ or —[CH=C($CH_3$)—]$_n$, where n may be, for example, from the range 2-50. Preferred alkyl contains 1-22 carbon atoms; preferred alkenyl and alkinyl each contains 2-22 carbon atoms, especially 3-22 carbon atoms.

Any alkyl moiety of more than one, especially more than 2 carbon atoms, or such alkyl or alkylene moieties which are part of another moiety, may be interrupted by a heterofunction such as O, S, COO, OCNR10, OCOO, OCONR10, NR10CNR10, or NR10, where R10 is H, $C_1$-$C_{12}$alkyl, $C_4$-$C_{12}$cycloalkyl. They can be interrupted by one or more of these spacer groups, one group in each case being inserted, in general, into a C—H or preferably into a carbon-carbon bond, with hetero-hetero bonds, for example O—O, S—S, NH—NH, etc., not occurring; if the interrupted alkyl is additionally substituted, the substituents are generally not α to the heteroatom. If two or more interrupting groups of the type —O—, —NR10-, —S— occur in one radical, they often are identical.

The term alkyl, whereever used, thus mainly embraces especially uninterrupted and, where appropriate, substituted $C_1$-$C_{22}$alkyl such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Alkoxy is alkyl-O—; alkylthio is alkyl-S—.

The term aryl or aromatic moiety, whereever used, mainly embraces $C_1$-$C_{18}$aromatic moieties, which may be heterocyclic rings containing, as part of the ring structure, one or more heteroatoms mainly selected from O, N and S; this preferably comprises monocyclic rings or polycyclic ring systems with the highest possible number of double bonds, such as preferably phenyl, naphthyl, anthrachinyl, anthracenyl or fluorenyl. Examples for hydrocarbon aryl or aromatics mainly are $C_6$-$C_{18}$ including phenyl, naphthyl, anthrachinyl, anthracenyl, fluorenyl; examples for heterocyclics ($C_1$-$C_{18}$) include those of the following table:

| ring structure | name | monovalent residue |
|---|---|---|
| | pyridine | pyridyl |
| | pyrimidine | pyrimidyl |
| | pyridazine | pyridazyl |
| | pyrazine | pyrazyl |
| | purine | purinyl |
| | pteridine | pteridyl |
| | thiophene | thiophenyl |
| | benzothiophene | benzothiophenyl |
| | pyrrol | pyrryl |
| | furane | furyl |
| | benzofurane | benzofuryl, |
| | dibenzofurane | dibenzofuryl |
| | indole | indyl |
| | carbazole | carbazolyl |
| | benzimidazole | benzimidazolyl |
| | benzopyrazole | benzopyrazolyl |
| | benzotriazole | benzotriazolyl |
| | imidazole | imidazolyl |
| | pyrazole | pyrazolyl |
| | triazole | triazolyl |
| including isomers such as 1,2,4-triazole (1,2,4-triazolyl), 1,2,3-triazole (1,2,3-triazolyl) | | |
| | tetrazole | tetrazolyl |
| | thiazole | thiazolyl |
| | | thienothienyl |
| | | dithiaindacenyl |
| | | chinolyl |

| ring structure | name | monovalent residue |
| --- | --- | --- |
| | isochinolyl | |
| | chinoxalyl | |
| | acridyl | | as well as azanaphthyl, phenanthrolyl, triazinyl, tetrahydronaphthyl, thienyl, pyrazolyl, imidazolyl,

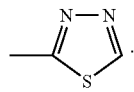

Substituents, if present, often are selected from halogen, $C_1$-$C_{18}$alkoxy, $C_1C_{18}$alkyl, $C_2$-$C_{18}$alkenyl, $C_2$-$C_{18}$alkynyl, $C_1$-$C_{18}$alkylthio, $C_1$-$C_{18}$acyl, $C_5$-$C_{10}$aryl, $C_4$-$C_{10}$heteroaryl, $C_3$-$C_{12}$cycloalkyl, $C_1$-$C_{18}$acyloxy, $C_5$-$C_{10}$aryloxy, $C_3$-$C_{12}$cycloalkyloxy, the above hydrocarbon moieties substituted by one or more R', or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O) R, S(O)OR, S(O)NHR, S(O)NRR', S(O)NH—NHR, S(O) NH—NRR', SiRR'R", PORR', PO(OR)R', PO(OR)$_2$, PO(NHR)$_2$, PO(NRR')$_2$, CN, $NO_2$, NHR, NRR', NH—NHR, NH—NRR', CONROH;

where R, R' and R" independently are selected from
 $C_1$-$C_{12}$alkyl, $C_1$-$C_{12}$haloalkyl, $C_2$-$C_8$alkenyl, $C_2$-$C_8$alkynyl, $C_5$-$C_{10}$aryl, $C_2$-$C_{18}$acyl, $C_3$-$C_{12}$cycloalkyl, such as from $C_1$-$C_6$alkyl, phenyl, cyclopentyl, cyclohexyl; and R may also be hydrogen.

Where residues are substituted, substituents usually bond to a carbon atom and are preferably selected from $C_1$-$C_{18}$alkoxy; $C_1$-$C_{18}$alkyl; said alkyl or alkoxy substituted by halogen, OH, COOH or CONH$_2$; said alkyl or alkoxy interrupted by O, S, COO or CONH; $C_2$-$C_8$alkenyl; $C_2$-$C_8$alkynyl; $C_4$-$C_{12}$cycloalkoxy; $C_4$-$C_{12}$cycloalkyl; OH; COOH; halogen; $C_1$-$C_{14}$aryl such as phenyl or naphthyl; said aryl substituted by $C_1$-$C_8$alkyl, $C_1$-$C_8$alkoxy, $C_1$-$C_8$haloalkyl $C_2$-$C_8$alkenyl, $C_2$-$C_8$alkynyl, $C_1$-$C_8$alkoxycarbonyl, $C_1$-$C_8$alkanoyloxy, nitro, halogen, OH, COOH, CONH$_2$; where saturated carbons also may be substituted by oxo (=O), adjacent substituents may be linked together, e.g. to form a carbocyclic, lactone, anhydride, cyclic ether such as oxethane or epoxy, or imide ring. Preferred substituents are halogen, aryl, alkyl, alkenyl, alkoxy.

Halogen denotes I, Br, Cl, F, preferably Cl, F, especially F. Haloalkyl denotes alkyl substituted by halogen; this includes perhalogenated alkyl such as perfluoroalkyl, especially $C_1$-$C_4$perfluoroalkyl, which is a branched or unbranched radical such as for example —CF$_3$, —CF$_2$CF$_3$, —CF$_2$CF$_2$CF$_3$, —CF(CF$_3$)$_2$, —(CF$_2$)$_3$CF$_3$, and —C(CF$_3$)$_3$.

The term alkenyl, whereever used, mainly embraces straight-chain or branched, especially uninterrupted and, where appropriate, substituted $C_2$-$C_{22}$alkyl such as vinyl, allyl, etc.

Alkynyl such as $C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic cyclic moieties include cycloalkyl, aliphatic heterocyclic moieties, as well as unsaturated variants thereof such as cycloalkenyl. Cycloalkyl such as $C_3$-$C_{18}$cycloalkyl, is preferably $C_3$-$C_{12}$cycloalkyl or said cycloalkyl substituted by one to three $C_1$-$C_4$alkyl groups, and includes cyclopropyl, cyclobutyl, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred. $C_3$-$C_{12}$cycloalkyl includes cyclopropyl, cyclobutyl, cyclopentyl, cyclohexyl, cycloheptyl, cyclooctyl, cyclononyl, cyclodecyl, cycloundecyl, cyclododecyl; preferred among these residues are $C_3$-$C_6$cycloalkyl as well as cyclododecyl, especially cyclohexyl. Further ring structures occurring are heterocyclic aliphatic rings usually containing 5 to 7 ring members, among them at least 1, especially 1-3, heteromoieties, usually selected from O, S, NR10, where R10 is as explained above for interrupting NR10-groups; examples include $C_4$-$C_{18}$cycloalkyl, which is interrupted by S, O, or NR10, such as piperidyl, tetrahydrofuranyl, piperazinyl and morpholinyl. Unsaturated variants may be derived from these structures by abstraction of a hydrogen atom on 2 adjacent ring members with formation of a double bond between them; an example for such a moiety is cyclohexenyl.

Alkoxy such as $C_1$-$C_{24}$alkoxy is a straight-chain or branched radical, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

Cycloalkoxy is, for example, cyclopentyloxy, cyclohexyloxy, cycloheptyloxy or cyclooctyloxy, or said cycloalkoxy substituted by one to three $C_1$-$C_4$alkyl, for example, methylcyclopentyloxy, dimethylcyclopentyloxy, methylcyclohexyloxy, dimethylcyclohexyloxy, trim ethylcyclohexyloxy, or tert-butylcyclohexyloxy.

Acyl stands for a residue of a sulfonic acid or especially organic carboxylic acid, which is formed formally by abstraction of the acid OH; examples are formyl, acetyl, propionyl, benzoyl. Generally, $C_1$-$C_{18}$ acyl stands for a radical X'—R$_{11}$, wherein X' is CO or SO$_2$ and R$_{11}$ is selected from monovalent aliphatic or aromatic organic residues, usually from molecular weight up to 300; for example, R$_{11}$ may be selected from $C_1$-$C_{18}$alkyl, $C_2$-$C_{18}$alkenyl, $C_5$-$C_{10}$aryl which may be unsubstituted or substituted by $C_1$-$C_8$alkyl or halogen or $C_1$-$C_8$alkoxy, $C_6$-$C_{15}$arylalkyl which may be unsubstituted or substituted in the aromatic part by $C_1$-$C_8$alkyl or halogen or $C_1$-$C_8$alkoxy, $C_4$-$C_{12}$cycloalkyl, and in case that X' is CO, R$_{11}$ may also be H. Acyl is preferably an aliphatic or aromatic residue of an organic acid —CO—R$_{11}$, usually of 1 to 30 carbon atoms, wherein R$_{11}$ embraces aryl, alkyl, alkenyl, alkynyl, cycloalkyl, each of which may be substituted or unsubstituted and/or interrupted as described elsewhere inter alia for alkyl residues, or R' may be H (i.e. COR' being formyl). Preferences consequently are as described for aryl, alkyl etc.; more preferred acyl residues are substituted or unsubstituted benzoyl, substituted or unsubstituted $C_1$-$C_{17}$alkanoyl or alkenoyl such as acetyl or propionyl or butanoyl or pentanoyl or hexanoyl, substituted or unsubstituted $C_5$-$C_{12}$cycloalkylcarbonyl such as cyclohexylcarbonyl.

Ligand L often conforms to the formula II $$D_1\text{-}G\text{-}D_2 \quad (II)$$

wherein G stands for a divalent organic bridging group or a direct bond and $D_1$ and $D_2$, each independently, stand for an organic moiety containing an electron donating heteroatom selected from nitrogen, sulphur and/or phosphorus.

Ligand A often conforms to the formula III $$D_3\text{-}G'\text{-}D_4 \quad (III)$$

wherein G' stands for an organic bridging group or a direct bond, $D_3$ stands for an organic moiety containing an electron donating heteroatom selected from nitrogen, oxygen, sulphur, phosphorus, and $D_4$ stands for an organic moiety containing an anionic heteroatom selected from nitrogen, sulphur;

which may, for certain ligands A, be formulated as formula IV

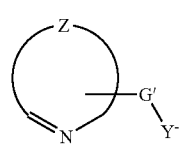

(IV)

wherein

Z is an organic bridging group forming, together with the nitrogen atom, an unsaturated or aromatic 4- to 8-membered ring, which optionally may be substituted, and $Y^-$ is an aliphatic or aromatic, cyclic or non-cyclic organic moiety binding to the central Cu atom by anionic nitrogen.

In preferred ligands of the formula III, G' stands for a direct bond;

$D_3$ stands for an unsaturated or aromatic heterocyclic moiety of 5 to 14 ring atoms, such as a tertiary aromatic amino moiety or a corresponding oxa or thia moiety;

$D_4$ stands for an anion of an unsaturated or aromatic N-heterocyclic moiety of 5 to 14 ring atoms;

or the ligand $D_3$-$G'$-$G_4$ stands for a system of at least 2 annealed rings of of 8 to 14 ring atoms according to the formula V

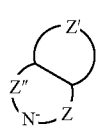

(V)

which optionally may be substituted, and wherein Z' is an organic bridging group containing at least one electron donating heteroatom selected from nitrogen, oxygen, sulphur, phosphorus, and forming, together with the carbon atoms it bonds to, an unsaturated or aromatic 4- to 8-membered ring, which optionally may be substituted; and wherein Z and Z'' independently are selected from organic bridging groups and a direct bond completing together, with the nitrogen atom, an unsaturated or aromatic 4- to 8-membered ring, which optionally may be substituted and wherein at least one of Z and Z'' is not a direct bond.

$D_3$ is often selected from pyridyl, pyrimidyl, pyridazyl, pyrazyl, pyranyl, cumaryl, pteridyl, thiophenyl, benzothiophenyl, furyl, benzofuryl, thiazolyl, thienothienyl, dithiaindacenyl, chinolyl, isochinolyl, chinoxalyl, acridyl, azanaphthyl, phenanthrolyl, triazinyl, thienyl,

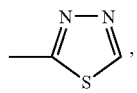

each of which is unsubstituted or substituted;

$D_4$ from anionic moieties as obtainable after N-deprotonation of a residue purinyl, pyrryl, indyl, carbazolyl, triazolyl, benzotriazolyl, pyrazolyl, benzopyrazolyl, imidazolyl, benzimidazolyl, tetrazolyl, each of which is unsubstituted or substituted;

or the ligand $D_3$-$G'$-$D_4$ is of the formula V, wherein Z' is an organic bridging group bonding to the 2 connecting carbon atoms and selected from NCHCHCH, CHNCHCH, NNCHCH, NCHNCH, NCHCHN, NNNCH, NNCHN, OCHCH, CHOCH, OCHN, SCHCH, SCHN, CHSCH, whose carbon atoms optionally may be substituted; and Z''—N—Z is an organic bridging group bonding to the 2 connecting carbon atoms and selected from NCHCH, CHNCH, NCHN, NNCH, NNN, whose carbon atoms, if present, optionally may be substituted;

especially where a heteroatom from $D_3$ or Z', and the anionic nitrogen, are in 1,3- or 1,4- or 1,5-position.

Preferred ligands L of the formula II are those wherein G stands for a divalent organic bridging group selected from $C_1$-$C_8$alkylene, $C_2$-$C_8$alkenylene, $C_2$-$C_8$alkinylene, O, S, SO, $SO_2$, O-interrupted $C_2$-$C_6$alkylene, phenylene, substituted phenylene, or for a direct bond; and $D_1$ and $D_2$, each independently, are selected from phosphinyl moieties of the formula VI $$P(D_5)(D_6)D_7\text{-} \quad (VI)$$

and $D_3$, where $D_3$ is an unsaturated or aromatic N-heterocyclic moiety of 5 to 14 ring atoms, such as a tertiary aromatic amino moiety; preferably $D_3$ is selected from pyridyl, pyrimidyl, pyridazyl, pyrazyl, pyranyl, cumaryl, pteridyl, thiophenyl, benzothiophenyl, furyl, benzofuryl, thiazolyl, thienothienyl, dithiaindacenyl, chinolyl, isochinolyl, chinoxalyl, acridyl, azanaphthyl, phenanthrolyl, triazinyl, thienyl,

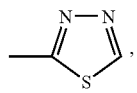

each of which is unsubstituted or substituted;

$D_5$ and $D_6$ independently are $C_1$-$C_8$alkyl, $C_2$-$C_8$alkenyl, $C_2$-$C_8$alkinyl, or preferably $C_4$-$C_{10}$aryl such as phenyl, each of which is unsubstituted or substituted; and $D_7$ is $C_1$-$C_8$alkylene, $C_2$-$C_8$alkenylene, $C_2$-$C_8$alkinylene, or preferably $C_4$-$C_{10}$arylene such as phenylene, each of which is unsubstituted or substituted;

especially where the electron donating heteroatoms are in 1,4-, 1,5-, 1,6-, 1,7-, 1,8- or 1,9-position.

A number of ligands of the present invention are novel compounds. The present invention therefore further pertains to the use of a 3-pyridyl-substituted 1,2,4-triazole of the below formulae as a ligand for the preparation of a transition metal complex such as a Cu, Fe, Ni, Ir, Rh, Ru, Pt, Pd complex;

as well as to a compound of the formula

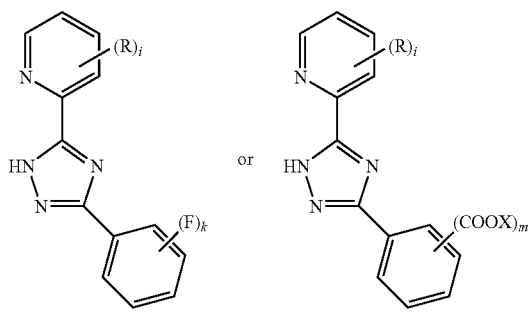

wherein
i and m independently are 0, 1 or 2;
k is from the range 3-5;
R independently is $C_1$-$C_{12}$alkyl, $C_2$-$C_8$alkenyl, halogen, nitro, amino, methoxy;
X is H, $C_1$-$C_{12}$alkyl or an equivalent of a cation such as Li+, Na+, K+, ½ Ca2+, ½ Mg2+, ½ Zn2+.

The above formulae only show one of the possible resonance/tautomeric forms of the present ligand A (or its protonated form), while other forms are possible as well and covered by the present invention.

Complexes and ligands of the present may conveniently be obtained in analogy to methods known in the art, e.g. as initially mentioned. For example, the preparation of Cu(I) complexes of the invention may start from suitable copper salts or copper complexes such as CuHal (where Hal stands for a halogenide anion such as chloride or bromide), $CuPF_6$ preferably as a complex with neutral ligands such as acetonitrile, etc., which is subsequently reacted with ligand L and ligand A, the latter preferably in its protonated (=neutral) form. The reaction usually takes place using an organic solvent or mixture of solvents, preferably under protection from oxygen. Workup follows standard procedures such as filtration, drying etc.

Ligands L are widely known in the art, many are commercially available.

Some of the protonated precursors for ligand A also are known in the art, other may be obtained in analogy to the known compounds, e.g. those described in US 2006/286404.

The present invention is also directed to an electronic device comprising the metal complex and its fabrication process. The electronic device can comprise at least one organic active material positioned between two electrical contact layers, wherein at least one of the layers of the device includes the metallic complex compound. The electronic device can comprise an anode layer (a), a cathode layer (e), and an active layer (c). Adjacent to the anode layer (a) is an optional hole-injecting/transport layer (b), and adjacent to the cathode layer (e) is an optional electron-injection/transport layer (d). Layers (b) and (d) are examples of charge transport layers.

The active layer (c) can comprise at least approximately 1 weight percent of metal complex of present invention.

In some embodiments, the active layer (c) may be substantially 100% of the metal complex because a host charge transporting material, such as $Alq_3$ is not needed. By "substantially 100%" it is meant that the metal complex is the only material in the layer, with the possible exception of impurities or adventitious by-products from the process to form the layer. Still, in some embodiments, the metal complex may be a dopant within a host material, which is typically used to aid charge transport within the active layer (c). The active layer (c), including any of the metal complexes, can be a small molecule active material, or a polymeric active material.

The device may include a support or substrate (not shown) adjacent to the anode layer (a) or the cathode layer (e). Most frequently, the support is adjacent the anode layer (a). The support can be flexible or rigid, organic or inorganic. Generally, glass or flexible organic films are used as a support. The anode layer (a) is an electrode that is more efficient for injecting holes compared to the cathode layer (e). The anode can include materials containing a metal, mixed metal, alloy, metal oxide or mixed-metal oxide. Suitable metal elements within the anode layer (a) can include the Groups 4, 5, 6, and 8-11 transition metals. If the anode layer (a) is to be light transmitting, mixed-metal oxides of Groups 12, 13 and 14 metals, such as indium-tin-oxide, may be used. Some non-limiting, specific examples of materials for anode layer (a) include indium-tin-oxide ("ITO"), aluminum-tin-oxide, gold, silver, copper, nickel, and selenium.

The anode layer (a) may be formed by a chemical or physical vapor deposition process or spin-cast process. Chemical vapor deposition may be performed as a plasma-enhanced chemical vapor deposition ("PECVD") or metal organic chemical vapor deposition ("MOCVD").

Physical vapor deposition can include all forms of sputtering (e. g., ion beam sputtering), e-beam evaporation, and resistance evaporation.

Specific forms of physical vapor deposition include rf magnetron sputtering or inductively-coupled plasma physical vapor deposition ("ICP-PVD"). These deposition techniques are well-known within the semiconductor fabrication arts.

A hole-transport layer (b) may be adjacent the anode. Both hole transporting small molecule compounds and polymers can be used.

Commonly used hole transporting molecules include: N,N'-diphenyl-N,N'-bis(3-methylphenyl)-[1,1'-biphenyl]-4, 4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis (9H-carbazol-9-yl)cyclobutane (DCZB), N,N,N',N'-tetrakis (4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), porphyrinic compounds, and combinations thereof.

Commonly used hole transporting polymers are polyvinylcarbazole, (phenylmethyl) polysilane, poly(3,4-ethylendioxythiophene) (PEDOT), and polyaniline. Hole-transporting polymers can be obtained by doping hole-transporting molecules such as those mentioned above into polymers such as polystyrene and polycarbonate.

The hole-injection/transport layer (b) can be formed using any conventional means, including spin-coating, casting, and printing, such as gravure printing. The layer can also be applied by ink jet printing, thermal patterning, or chemical, or physical vapor deposition.

Usually, the anode layer (a) and the hole-injection/transport layer (b) are patterned during the same lithographic operation. The pattern may vary as desired. The layers can be formed in a pattern by, for example, positioning a patterned mask or resist on the first flexible composite barrier structure prior to applying the first electrical contact layer material. Alternatively, the layers can be applied as an overall layer (also called blanket deposit) and subsequently patterned using, for example, a patterned resist layer and wet-chemical or dry-etching techniques. Other processes for patterning that are well known in the art can also be used. When the electronic devices are located within an array, the anode layer (a) and hole injection/transport layer (b) typically are formed into substantially parallel strips having lengths that extend in substantially the same direction.

The active layer (c) may comprise the metal complexes described herein. The particular material chosen may depend on the specific application, potentials used during operation, or other factors. The active layer (c) may comprise a host material capable of transporting electrons and/or holes, doped with an emissive material that may trap electrons, holes, and/or excitons, such that excitons relax from the emissive material via a photoemissive mechanism. Active layer (c) may comprise a single material that combines transport and emissive properties. Whether the emissive material is a dopant or a major constituent, the active layer may comprise other materials, such as dopants that tune the emission of the emissive material. Active layer (c) may include a plurality of emissive materials capable of, in combination, emitting a desired spectrum of light. Examples of phosphorescent emissive materials include the metal complexes of the present invention. Examples of fluorescent emissive materials include DCM and DMQA. Examples of host materials include $Alq_3$, CBP and mCP. Examples of emissive and host materials are disclosed in U.S. Pat. No. 6,303,238, which is incorporated by reference in its entirety.

The active layer (c) can be applied from solutions by any conventional technique, including spin coating, casting, and printing. The active organic materials can be applied directly by vapor deposition processes, depending upon the nature of the materials.

Optional layer (d) can function both to facilitate electron injection/transport, and also serve as a buffer layer or confinement layer to prevent quenching reactions at layer interfaces. More specifically, layer (d) may promote electron mobility and reduce the likelihood of a quenching reaction if layers (c) and (e) would otherwise be in direct contact. Examples of materials for optional layer (d) include metal-cheated oxinoid compounds (e. g., tris(8-hydroxyquinolato) aluminum ($Alq_3$) or the like); phenanthroline-based compounds (e. g., 2,9-dimethyl-4,7-diphenyl-1,10-phenanthroline ("DDPA"), 4,7-diphenyl-1,10-phenanthroline ("DPA"), or the like; azole compounds (e. g., 2-(4-biphenylyl)-5-(4-t-butylphenyl)-1,3,4-oxadiazole ("PBD") or the like, 3-(4-biphenylyl)-4-phenyl-5-(4-t-butylphenyl)-1,2,4-triazole ("TAZ") or the like; other similar compounds; or any one or more combinations thereof. Alternatively, optional layer (d) may be inorganic and comprise BaO, LiF, $Li_2O$, or the like.

The electron injection/transport layer (d) can be formed using any conventional means, including spin-coating, casting, and printing, such as gravure printing. The layer can also be applied by ink jet printing, thermal patterning, or chemical or physical vapor deposition.

The cathode layer (e) is an electrode that is particularly efficient for injecting electrons or negative charge carriers. The cathode layer (e) can be any metal or nonmetal having a lower work function than the first electrical contact layer (in this case, the anode layer (a)). Materials for the second electrical contact layer can be selected from alkali metals of Group 1 (e. g., Li, Na, K, Rb, Cs), the Group 2 (alkaline earth) metals, the Group 12 metals, the rare earths, the lanthanides (e. g. , Ce, Sm, Eu, or the like), and the actinides. Materials, such as aluminum, indium, calcium, barium, yttrium, and magnesium, and combinations thereof, may also be used. Li-containing organometallic compounds, LiF, and $Li_2O$ can also be deposited between the organic layer and the cathode layer to lower the operating voltage. Specific non-limiting examples of materials for the cathode layer (e) include barium, lithium, cerium, cesium, europium, rubidium, yttrium, magnesium, or samarium.

The cathode layer (e) is usually formed by a chemical or physical vapor deposition process. In general, the cathode layer will be patterned, as discussed above in reference to the anode layer (a) and optional hole injecting layer (b). If the device lies within an array, the cathode layer (e) may be patterned into substantially parallel strips, where the lengths of the cathode layer strips extend in substantially the same direction and substantially perpendicular to the lengths of the anode layer strips.

Electronic elements called pixels are formed at the cross points (where an anode layer strip intersects a cathode layer strip when the array is seen from a plan or top view).

In other embodiments, additional layer (s) may be present within organic electronic devices. For example, a layer (not shown) between the hole injecting layer (b) and the active layer (c) may facilitate positive charge transport, band-gap matching of the layers, function as a protective layer, or the like. Similarly, additional layers (not shown) between the electron injecting layer (d) and the cathode layer (e) may facilitate negative charge transport, band-gap matching between the layers, function as a protective layer, or the like. Layers that are known in the art can be used. Some or all of the layers may be surface treated to increase charge carrier transport efficiency. The choice of materials for each of the component layers may be determined by balancing the goals of providing a device with high device efficiency with the cost of manufacturing, manufacturing complexities, or potentially other factors.

The charge transport layers (b) and (d) are generally of the same type as the active layer (c). More specifically, if the active layer (c) has a small molecule compound, then the charge transport layers (b) and (d), if either or both are present, can have a different small molecule compound. If the active layer (c) has a polymer, the charge transport layers (b) and (d), if either or both are present, can also have a different polymer. Still, the active layer (c) may be a small molecule compound, and any of its adjacent charge transport layers may be polymers.

Each functional layer may be made up of more than one layer. For example, the cathode layer may comprise a layer of a Group I metal and a layer of aluminum. The Group I metal may lie closer to the active layer (c), and the aluminum may help to protect the Group I metal from environmental contaminants, such as water.

Although not meant to limit, the different layers may have the following range of thicknesses: inorganic anode layer (a), usually no greater than approximately 500 nm, for example, approximately 50-200 nm; optional hole-injecting layer (b), usually no greater than approximately 100 nm, for example, approximately 50-200 nm; active layer (c), usually no greater than approximately 100 nm, for example, approximately 10-80 nm; optional electron-injecting layer (d), usually no greater than approximately 100 nm, for example, approximately 10-80 nm; and cathode layer (e), usually no greater than approximately 1000 nm, for example, approximately 30-500 nm. If the anode layer (a) or the cathode layer (e) needs to transmit at least some light, the thickness of such layer may not exceed approximately 100 nm.

The location of the electron-hole recombination zone in the device, and thus the emission spectrum of the device, can be affected by the relative thickness of each layer. For example, when a potential light-emitting compound, such as Alq$_3$ is used in the electron transport layer (d), the electron-hole recombination zone can lie within the Alq$_3$ layer.

The emission would then be that of Alq$_3$, and not a desired sharp emission. Thus, the thickness of the electron-transport layer should be chosen so that the electron-hole recombination zone lies within the light-emitting layer (i. e., active layer (c)). The desired ratio of layer thicknesses can depend on the exact nature of the materials used.

The efficiency of the devices made with metal complexes can be further improved by optimizing the other layers in the device. For example, more efficient cathodes such as Ca, Ba, Mg/Ag, or LiF/Al can be used. Shaped substrates and hole transport materials that result in a reduction in operating voltage or increase quantum efficiency are also applicable.

Additional layers can also be added to tailor the energy levels of the various layers and facilitate electroluminescence.

Depending upon the application of the electronic device, the active layer (c) can be a light-emitting layer that is activated by a signal (such as in a light-emitting diode) or a layer of material that responds to radiant energy and generates a signal with or without an applied potential (such as detectors or voltaic cells). Examples of electronic devices that may respond to radiant energy are selected from photoconductive cells, photoresistors, photoswitches, phototransistors, and phototubes, and photovoltaic cells. After reading this specification, skilled artisans will be capable of selecting material (s) that for their particular applications.

The electroluminescent devices may be employed for full color display panels in, for example, mobile phones, televisions and personal computer screens. Accordingly the present invention relates also to a device selected from stationary and mobile displays, such as displays for computers, mobile phones, laptops, pdas, TV sets, displays in printers, kitchen equipment, billboards, lightings, information boards and destination boards in trains and buses, containing an organic light emitting diode according to the present invention.

In OLEDs, electrons and holes, injected from the cathode (e) and anode (a) layers, respectively, into the photoactive layer (c), form negative and positively charged polarons in the active layer (c). These polarons migrate under the influence of the applied electric field, forming a polaron exciton with an oppositely charged species and subsequently undergoing radiative recombination. A sufficient potential difference between the anode and cathode, usually less than approximately 20 volts, and in some instances no greater than approximately 5 volts, may be applied to the device. The actual potential difference may depend on the use of the device in a larger electronic component. In many embodiments, the anode layer (a) is biased to a positive voltage and the cathode layer (e) is at substantially ground potential or zero volts during the operation of the electronic device. A battery or other power source (s) may be electrically connected to the electronic device as part of a circuit.

In other embodiments, the metal complex compound can be used as a charge transport material in layer (b) or (d).

The compound does not need to be in a solid matrix diluent (e. g., host charge transport material) when used in layer (b) (c), or (d) in order to be effective. A layer greater than approximately 1% by weight of the metal complex compound, based on the total weight of the layer, and up to substantially 100% of the complex compound can be used as the active layer (c). Additional materials can be present in the active layer (c) with the complex compound. For example, a fluorescent dye may be present to alter the color of emission.

A diluent may also be added. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the complex compound is generally present in a small amount, usually less than 20% by weight, preferably less than 10% by weight, based on the total weight of the layer.

The metallic complexes may be used in applications other than electronic devices. For example, the complexes may be used as catalysts or indicators (e. g., oxygen-sensitive indicators, phosphorescent indicators in bioassays, or the like).

The following examples are for illustrative purposes only and are not to be construed to limit the instant invention in any manner whatsoever. Room temperature (r.t.) depicts a temperature in the range 20-25° C.; over night denotes a time period in the range 12-16 hours.

Percentages are by weight unless otherwise indicated.

Abbreviations used in the examples or elsewhere:

| | |
|---|---|
| DMF | dimethylformamide |
| THF | tetrahydrofuran |
| DCM | dichloromethane |
| MS | mass spectrometry |
| HRMS | high resolution mass spectrometry |
| ESI | electrospray ionization |
| GC | gas chromatography |
| NMR | nuclear magnetic resonance |
| PMMA | poly methylmethacrylate |
| PVK | poly vinylcarbazole |

EXPERIMENTAL SECTION

Synthesis of Ligands

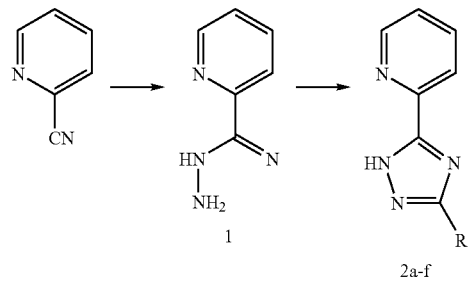

-continued

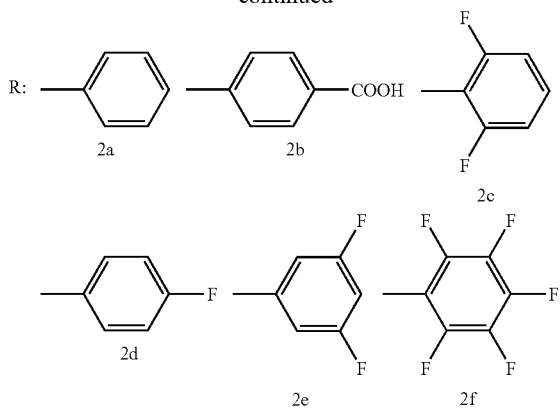

Synthesis and Characterization. All reagents are analytical grade and used as received. Solvents are purified according to the standard procedures. All reactions are performed under inert atmosphere (Schlenk-line techniques), except where noted. All column chromatography (CC) is performed with silica gel 60 (particle size 63-200 μm, 230-400 mesh, Merck) using common flash procedures.

(Pyridine-2-yl)amidrazone (1)—After melting 10.4 g (0.10 mol) of 2-cyanopyridine with gentle heating, 5.3 mL (5.5 g, 0.11 mol) of hydrazine monohydrate is added yielding a cloudy mixture. Ethanol (~5 mL) is added until the mixture becomes clear and the resulting solution is stirred overnight at room temperature, causing a gel-like product to form. All solvents are removed under reduced pressure and the solid is suspended in petroleum ether (50 mL), cooled in an ice bath and filtered, washing with cold petroleum ether, yielding 9.9 g (73%) of the amidrazone. The solid may be used without further purification or crystallized from toluene. Mp: 94-96° C. (Lit. 95-96° C.). $^1$H NMR (CDCl$_3$, 300 MHz): δ 8.50 (d, J=4.1 Hz, 1 H, Ar), 8.00 (d, J=8.0 Hz, 1 H, Ar), 7.67 (t, J=6.2 Hz, 1 H, Ar), 7.24 (d, J=6.2 Hz), 5.39 (s, 1 H, NH$_2$), 4.60 (s, 1 H, NH$_2$).

Lit.: F. H. Case, *Journal of Organic Chemistry* 1965, 30, 931.

Pyridine-2-yl-1,2,4-triazoles (2a-2f)—General Procedure—To a flame-dried, nitrogen purged 30 mL Schlenk tube was added of (pyridine-2yl)amidrazone (2.0 g, 15 mmol) and sodium carbonate (1.6 g, 15 mmol). The flask was evacuated and gently heated. After cooling, the flask was purged with nitrogen. Next, 15 mL of dry dimethylacetamide (DMAA) and 5 mL of dry THF was added, yielding a pale yellow suspension that was cooled to 0° C. In a separate, dry 10 mL Schlenk flask, 15 mmol of the appropriate acid chloride was dissolved in 5 mL of DMAA. This solution was then added to pre-cooled amidrazone mixture dropwise, which caused it to turn bright yellow. The mixture was slowly warmed to room temperature and stirred for an additional 5 h, yielding a thick yellow mixture. The contents were filtered, and the solid washed with water and EtOH and the resulting pale yellow solid allowed to air dry. The solid was suspended in 20 mL of ethylene glycol and heated to 190° C. for 30 min., yielding a pale yellow solution. Upon cooling to room temperature, a white solid formed and was collected on a glass frit, washing with deionized water. The solid was dried under vacuum and used without further purification.

2-(5-Phenyl-2H-1,2,4-triazol-3-yl)-pyridine (2a)—Benzoyl chloride. Yield: 63%. Mp: 212-214° C. (Lit.: 212° C.).

$^1$H NMR (300 MHz, DMSO): δ 8.73 (d, 1 H, J=4.3 Hz), 8.18 (d, 1 H, J=7.8 Hz), 8.10 (d, 1 H, J=7.0 Hz), 8.02 (t, 1 H, J=7.6 Hz), 7.60-7.40 (m, 4 H).

Lit.: R. Hage, R. Prins, J. G. Haasnoot, J. Reedijk, J. G. Vos, *Journal of the Chemical Society-Dalton Transactions* 1987, 1389.

4-(5-Pyridin-2-yl-1H-1,2,4-triazol-3-yl)-benzoic acid (2b)—4-(chlorocarbonyl)benzoic acid. Yield: 55%. $^1$H NMR (300 MHz, DMSO): δ 8.77 (d, 1H, J=4.8 Hz); 8.32 (d, 1H, J=7.8Hz); 8.27-8.16 (m, 3H); 8.08 (d, 1H, J=8.3 Hz); 7.70 (dd, 1H, J=5.3 Hz, J=7.3 Hz); 5.45 (s, 1H).

2-[5-(2,6-Difluoro-phenyl)-2H!-1,2,4-triazol-3-yl]-pyridine (2c)—2,6-difluorobenzoyl chloride. Off-white powder. Yield: 45%. Mp: 181-183° C. $^1$H NMR (300 MHz, DMSO): δ 9.18 (s, 1H), 8.74 (d, 1H, J=4.3 Hz), 8.12 (d, 1H, J=7.8 Hz), 8.01 (t, 1H, J=7.6 Hz), 7.60 (m, 2H), 7.28 (t, 2H, J=8.1 Hz).

2-[5-(4-Fluoro-phenyl)-2H-1,2,4-triazol-3-yl]-pyridine (2d)—4-difluorobenzoyl chloride. Off-white white powder. Yield: 72%. Mp: 241-243° C. $^1$H NMR (300 MHz, DMSO): δ 14.90 (s, 1H), 8.73 (d, 1H, J=4.33 Hz), 8.21-8.07 (m, 3H), 8.02 (dt, 1H, J=7.84 Hz), 7.55 (dd, 1H, J=6.66 Hz), 7.35 (t, 2H, J=8.84 Hz).

2-[5-(3,5-Difluoro-phenyl)-2H-1,2,4-triazol-3-yl]-pyridine (2e)—3,5-difluorobenzoyl chloride. Off-white powder. Yield: 68%. Mp: 254-257° C. $^1$H NMR (300 MHz, DMSO): δ 15.09 (s, 1H), 7.68-7.59 (m, 1H), 8.18 (d, 1H, J=7.8 Hz), 8.04 (dt, 1H, J=1.1 Hz, J=7.7 Hz), 7.75-7.52 (m, 3H), 7.36 (t, 1H, J=9.3 Hz).

2-[5-(2,3,4,5,6-pentafluoro-phenyl)-2H-1,2,4-triazol-3-yl]-pyridine (2f)—Pentafluorobenzoyl chloride. Tan solid. Yield: 60%. The product could be used without further purification or analytical purity could be obtained by sublimation (120° C., oil pump) to yield a white solid. Mp: >195° C. (dec.). $^1$H NMR (300 MHz, DMSO): δ 8.75 (d, 1 H, J=4.4 Hz), 8.11 (d, 1 H, J=7.8 Hz), 8.03 (dt, 1 H, J=1.5 Hz, J=7.8 Hz), 7.57 (dd, 1 H, J=5.2 Hz, J=6.3 Hz).

Synthesis of Complexes of the Type [Cu(PP) (NN)]

(1) Cu(DPEphos)(Phptp). (NN=2-(5-Phenyl-2H-1,2,4-triazol-3-yl)-pyridine) A typical procedure is as follows. A mixture of [Cu(CH$_3$CN)$_4$]PF$_6$ (141 mg, 0.26 mmol) and bis [2-(diphenylphosphino)phenyl]ether (DPEphos; 114.5 mg, 0.26 mmol) in 20 mL of dry THF was stirred at room temperature for 1 h under N$_2$ and then treated with a solution of 3-Phenyl-pyridin-2-yl-1,2,4-triazole (Phptp; 58.2 mg, 0.26 mmol) in 10 mL of THF. This reaction mixture was stirred for an additional 4 h and filtered and the clear green filtrate was vacuumed. The residue was purified by silicon chromatography used ethyl acetate/methanol=20:1 to get white product, yield 150 mg (70%). MS (ESI+, MeOH): m/z 823.1 ([M+H]$^+$, 30). Elemental Analysis: C: 61.31 H: 4.07 N: 5.19 (found); C: 61.67 H: 4.16 N: 5.64 (calculated).

The procedures for the synthesis of other neutral Cu(I) complexes were essentially identical to that described in (1). Only the quantities of ligand that were used, the product yields, and the MS are given.

(2) Cu(DPEphos)(COOHPhptp). (NN=4-(5-Pyridin-2-yl-1H-1,2,4-triazol-3-yl)-benzoic acid) (80.3 mg, 0.30 mmol). Yield: 210 mg, (81%). HRMS cacld for C$_{50}$H$_{37}$CuN$_4$O$_3$P$_2$ 867.3473([M+H]$^+$); found 867.1710.

A protonated form of this compound is obtained on addition of mineral acid (e.g. HCl, H$_2$SO$_4$; see FIG. 8).

(3) Cu(DPEphos)(2FPhptp). (NN=2-[5-(2,6-Difluoro-phenyl)-2H-1,2,4-triazol-3-yl]-pyridine) (56.4 mg, 0.22 mmol). Yield: 135 mg, (71%). MS (ESI+, MeOH): m/z 859.3 ([M+H]$^+$, 30). HRMS calcd for C$_{49}$H$_{35}$CuF$_2$N$_4$OP$_2$ 859.3187 ([M+H]$^+$); found 859.1823

(4) Cu(DPEphos)(FPhptp). (NN=2-[5-(4-Fluoro-phenyl)-2H-1,2,4-triazol-3-yl]-pyridine) (257.2 mg, 1.0 mmol). Yield: 630 mg, (75%). MS (ESI+, MeCN/CHCl$_3$): m/z 841.4 ([M+H]$^+$, 25). Elemental Analysis: C: 69.52 H: 4.57 N: 6.49 (found); C: 69.95 H: 4.31 N: 6.66 (calculated).

(5) Cu(DPEphos)(3,5-2FPhptp). (NN=2-[5-(3,5-Difluoro-phenyl)-2H-1,2,4-triazol-3-yl]-pyridine, 256.6 mg, 0.94 mmol). Yield: 570 mg (72%). MS (ESI+, MeOH): m/z 859.3 ([M+H]$^+$, 30).

(6) Cu(DPEphos)(5FPhptp). (NN=2-[5-(2,3,4,5,6-pentafluoro-phenyl)-2H-1,2,4-triazol-3-yl]-pyridine) (581.6 mg, 1.86 mmol). Yield: 965 mg (57%). MS (ESI+, MeCN/CHCl$_3$): m/z 642.3 ([M+H]$^+$, 40).). HRMS cacld for C$_{49}$H$_{32}$CuF$_5$N$_4$OP$_2$ 913.1268 ([M+H]$^+$); found 913.1340

(7) Cu(DPEphos)(Pta). (NN=2-(5-Phenyl-3H-1,2,3-triazol-4-yl)-pyridine) (163.7 mg 1.12 mmol). Yield: 569 mg (68%). MS (ESI+, MeOH): m/z 747.4 ([M+H]$^+$, 30).

(8) Cu(DPEphos)(Pbi). NN=2-Pyridin-2-yl-1H-benzimidazole) (324.6 mg, 1.66 mmol). Yield: 700 mg (53%). MS (ESI+, MeCN/CHCl$_3$): m/z 796.4 ([M+H]$^+$, 40).

(9) Cu(DPEphos)(Pid). (NN=2-(1H-Imidazol-2-yl)-pyridine) (260 mg, 1.79 mmol). Yield: 1200 mg (50%). MS (ESI+, MeCN/CHCl$_3$): m/z 746.3 ([M+H]$^+$, 100). HRMS cacld for C$_{44}$H$_{34}$CuN$_3$OP$_2$ 746.2538 ([M+H]$^+$); found 746.1546.

(10) Cu(DPEphos)(Aza). (NN=1H-Pyrrolo[2,3-b]pyridine) (123.6 mg, 1.02 mmol). Yield: 366 mg (51%). MS (ESI+, MeCN/CHCl$_3$): m/z 719.4 ([M+H]$^+$, 15). HRMS cacld for C$_{43}$H$_{33}$CuN$_2$OP$_2$ 719.2284 ([M+H]$^+$); found 719.1437.

(11) Cu(PhBisBI)(Pbi). (NN=2-Pyridin-2-yl-1H-benzimidazole) MS (ESI+, MeCN/CHCl$_3$): m/z 720.3 ([M+H]$^+$, 15). HRMS cacld for C$_{44}$H$_{30}$CuN$_7$ 719.1859 ([M]$^+$); found 719.1846.

(12) Cu(BDPEphos)(3,5-2FPhptp). (NN=2-[5-(3,5-Difluoro-phenyl)-2H-1,2,4-triazol-3-yl]-pyridine. Yield: 1.25 g (46%). MS (ES+, THF): m/z 899.05 ([M+H]$^+$, 13).

(13) Cu(DPEphos)(3,5-2F)Pta) (NN=2-(5-Phenyl-3H-1,2,3-triazol-4-yl)-pyridine. MS (ES+, THF): m/z 859.155.

(14) Cu(DPEphos)(4-MeOPhptp). (NN=2-[5-(4-methoxy-phenyl)-2H-1,2,4-triazol-3-yl]-pyridine. MS (ES+, THF): m/z 853.1908.

The compounds are soluble in THF, Toluene, DCM. Characterization has been done by NMR, MS and Xray. Formulae of the above compounds (numbers as in the above examples) are compiled in the following table:

| NO. | CU(I) Complexes Molecules | MS Info |
|---|---|---|
| 1 | 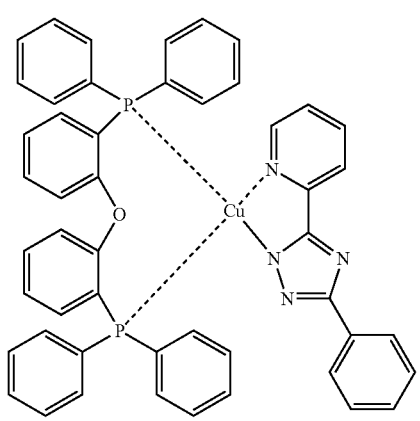 | Molecular Formula = C$_{49}$H$_{37}$CuN$_4$OP$_2$<br>Formula Weight = 823.337802<br>Monoisotopic Mass = 822.173859 Da |
| 2 | 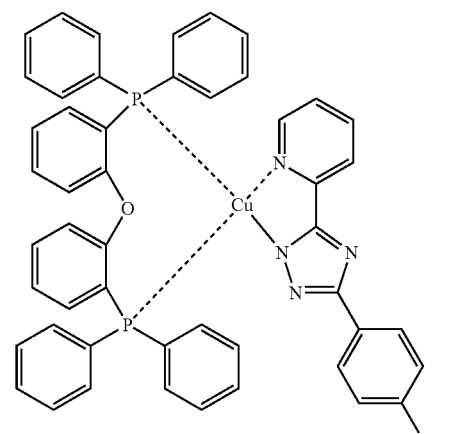 | Molecular Formula = C50H37CuN4O3P2<br>Formula Weight = 867.347304<br>Monoisotopic Mass = 866.163689 Da |

-continued
| NO. | CU(I) Complexes Molecules | MS Info |
|---|---|---|
| 3 | 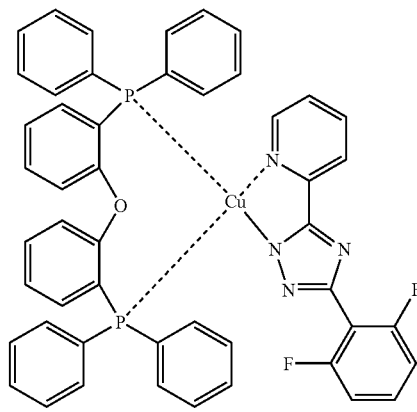 | Molecular Formula = C49H35CuF2N4OP2<br>Formula Weight = 859.3187284<br>Monoisotopic Mass = 858.155015 Da |
| 4 | 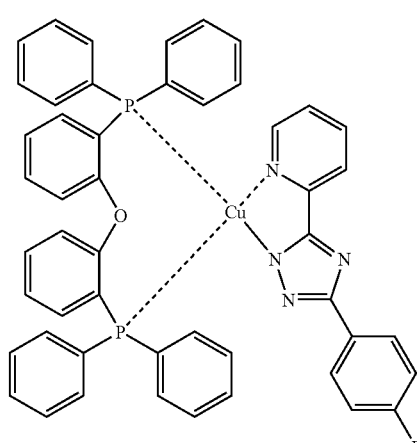 | Molecular Formula = C49H36CuFN4OP2<br>Formula Weight = 841.3282652<br>Monoisotopic Mass = 840.164437 Da |
| 5 | 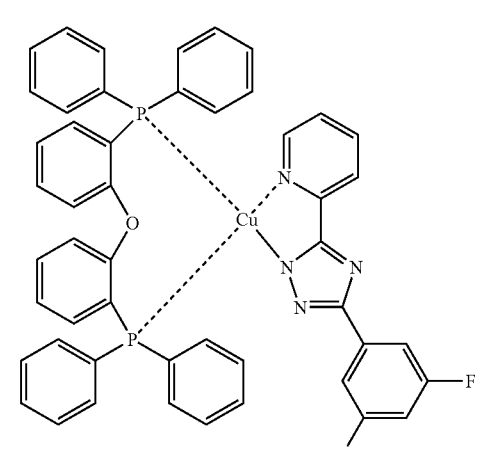 | Molecular Formula = $C_{49}H_{35}CuF_2N_4OP_2$<br>Formula Weight = 859.3187284<br>Monoisotopic Mass = 858.155015 Da |

-continued
| NO. | CU(I) Complexes Molecules | MS Info |
|---|---|---|
| 6 | 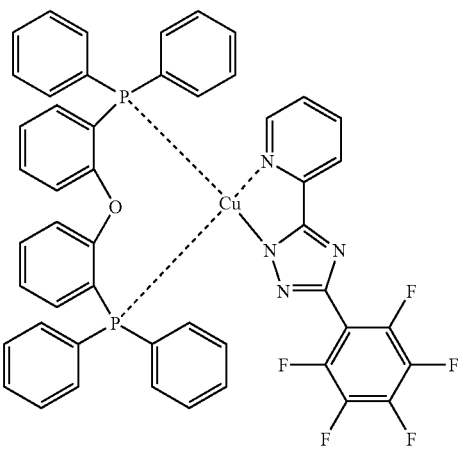 | Molecular Formula = $C_{49}H_{32}CuF_5N_4OP_2$<br>Formula Weight = 913.29012<br>Monoisotopic Mass = 912.126751 Da |
| 7 | 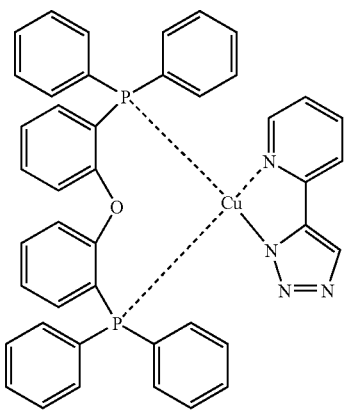 | Molecular Formula = $C_{43}H_{33}CuN_4OP_2$<br>Formula Weight = 747.241844<br>Monoisotopic Mass = 746.14256 Da |
| 8 | 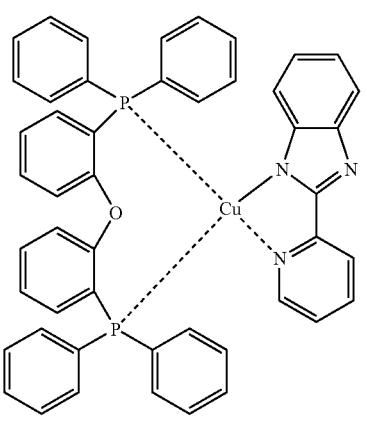 | Molecular Formula = C48H36CuN3OP2<br>Formula Weight = 796.312464<br>Monoisotopic Mass = 795.162961 Da |

-continued
| NO. | CU(I) Complexes Molecules | MS Info |
|---|---|---|
| 9 | 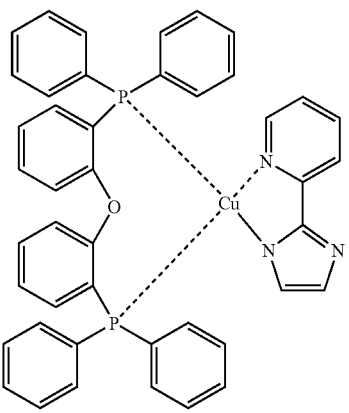 | Molecular Formula = $C_{44}H_{34}CuN_3OP_2$<br>Formula Weight = 746.253784<br>Monoisotopic Mass = 745.147311 Da |
| 10 | 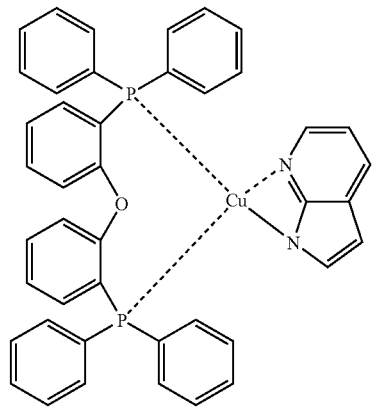 | Molecular Formula = $C_{43}H_{33}CuN_2OP_2$<br>Formula Weight = 719.228444<br>Monoisotopic Mass = 718.136412 Da |
| 11 | 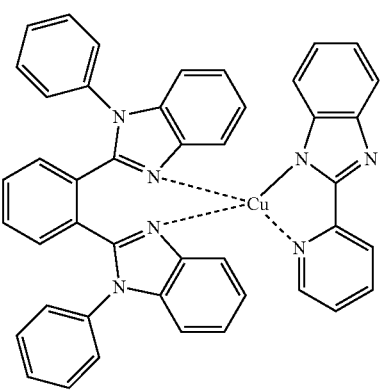 | Molecular Formula = $C_{44}H_{30}CuN_7$<br>Formula Weight = 720.3019<br>Monoisotopic Mass = 719.185869 Da |

-continued

| NO. | CU(I) Complexes Molecules | MS Info |
|---|---|---|
| 12 | | Molecular Formula = $C_{52}H_{39}CuF_2N_4OP_2$<br>Formula Weight = 899.41 |
| 13 | | Molecular Formula = C49H35CuF2N4OP2<br>Formula Weight = 859.1623<br>Monoisotopic Mass = 859.1554 Da |
| 14 | | Molecular Formula = C50H39CuN4O2P2<br>Formula Weight = 853.3637<br>Monoisotopic Mass = 853.1908 |

Photophysics. Absorption spectra are measured on a Varian Cary 5000 double-beam UV-Vis-NIR spectrometer and baseline corrected. Steady-state emission spectra are recorded on a HORIBA Jobin-Yvon IBH FL-322 Fluorolog 3 spectrometer equipped with a 450 W xenon arc lamp, double grating excitation and emission monochromators (2.1 nm/mm dispersion; 1200 grooves/mm) and a Hamamatsu R928 photomultiplier tube or a TBX-4-X single-photon-counting detector. Emission and excitation spectra are corrected for source intensity (lamp and grating) and emission spectral response (detector and grating) by standard correction curves. Time-resolved measurements are performed using the time-correlated single-photon counting (TCSPC) option on the Fluorolog 3. NanoLEDs (295 or 402 nm; FWHM<750 ps) with repetition rates between 10 kHz and 1 MHz are used to excite the sample. The excitation sources are mounted directly on the sample chamber at 90° to a double grating emission monochromator (2.1 nm/mm dispersion; 1200 grooves/mm) and collected by a TBX-4-X single-photon-counting detector. The photons collected at the detector are correlated by a time-to-amplitude converter (TAC) to the excitation pulse. Signals are collected using an IBH DataStation Hub photon counting module and data analysis is performed using the commercially available DAS6 software (HORIBA Jobin Yvon IBH). The goodness of fit is assessed by minimizing the reduced chi squared function ($X^2$) and visual inspection of the weighted residuals. Spectrometry and elemental (CHN) analyses are performed in the Department of Chemistry, University of Munster. Electrospray ionization (ESI) mass spectra are recorded on a Bruker Daltonics (Bremen, Germany) MicroTof with loop injection. The colorless single crystals of Cu(I) complexes are obtained by vapor diffusion of diethyl ether in to the solution of Cu(I) complexes in tetrahydrofuran at room temperature.

[Cu(CH$_3$CN)$_4$]PF$_6$ is prepared following literature procedure: G. J. Kubas, *Inorg. Synth.* 1979, 19, 90.

Polymer based applications of the present complexes are realized after incorporation in a polymer matrix by dissolution and evaporation of the solvent. Electroluminescent devices containing the present complex in a PVK layer, or layers for spectral testing are obtained using this method.

Figure 1:
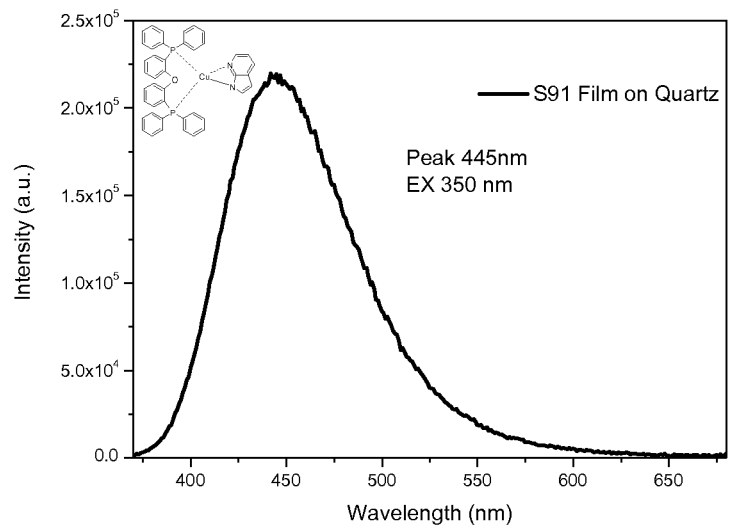
FIG. 1-7 show emission spectra of the compounds as indicated.
Figure 2:
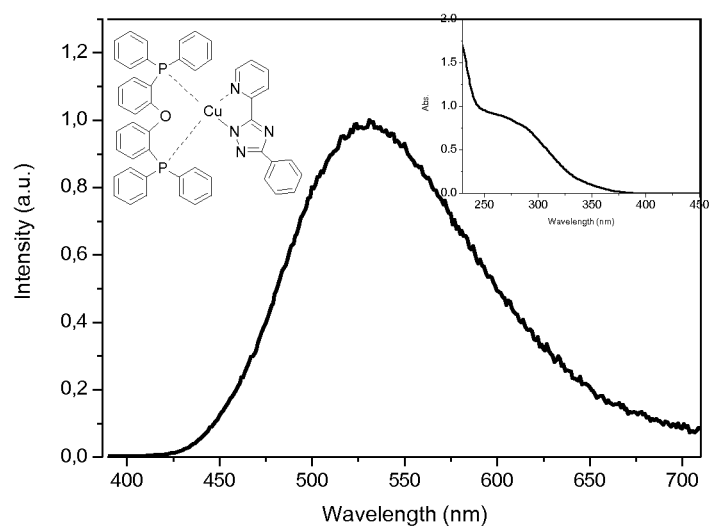
Figure 3:
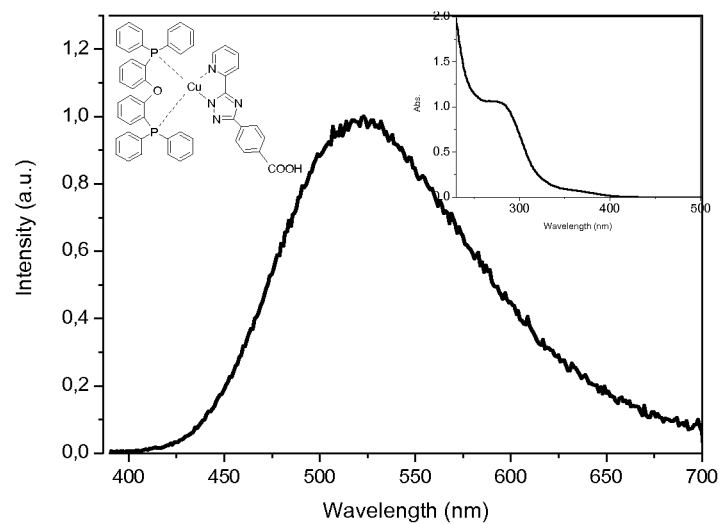
Figure 4:
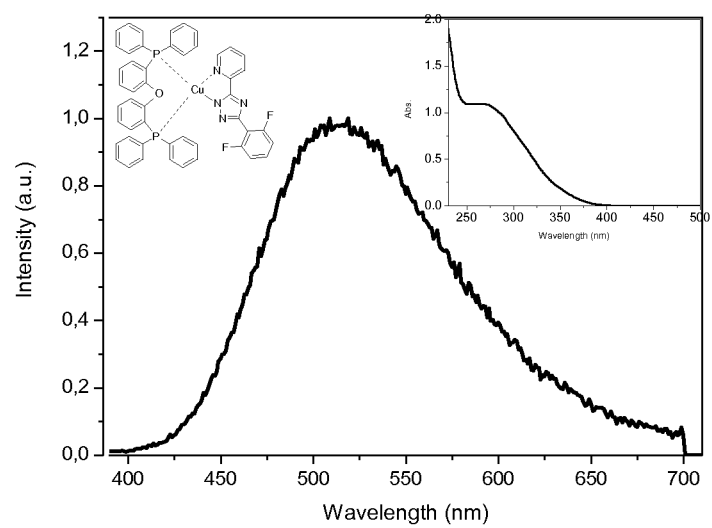
Figure 5:
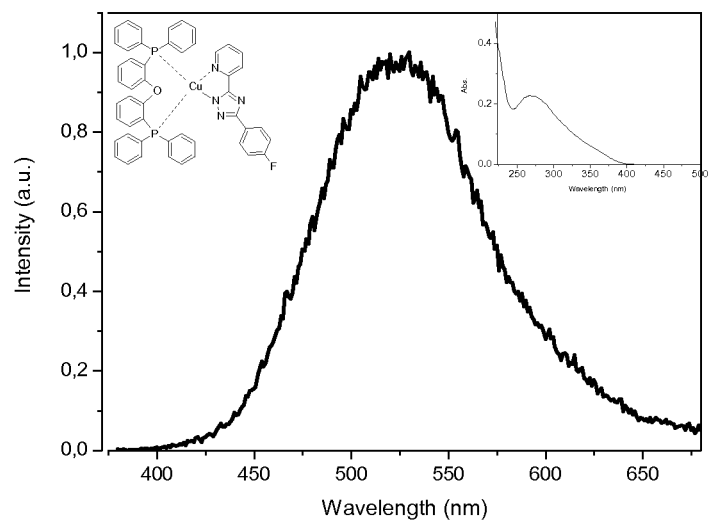
Figure 6:
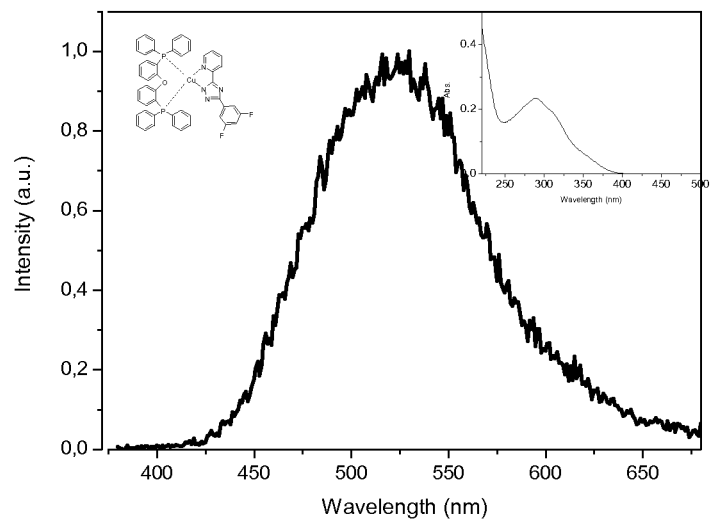
Figure 7:
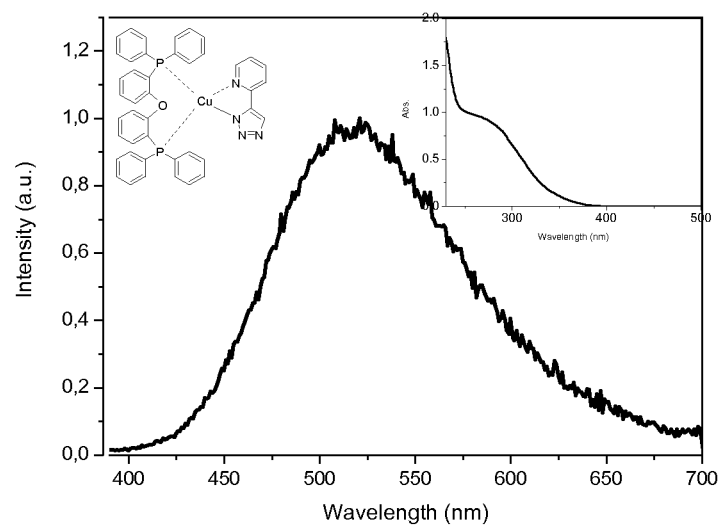
Figure 8:
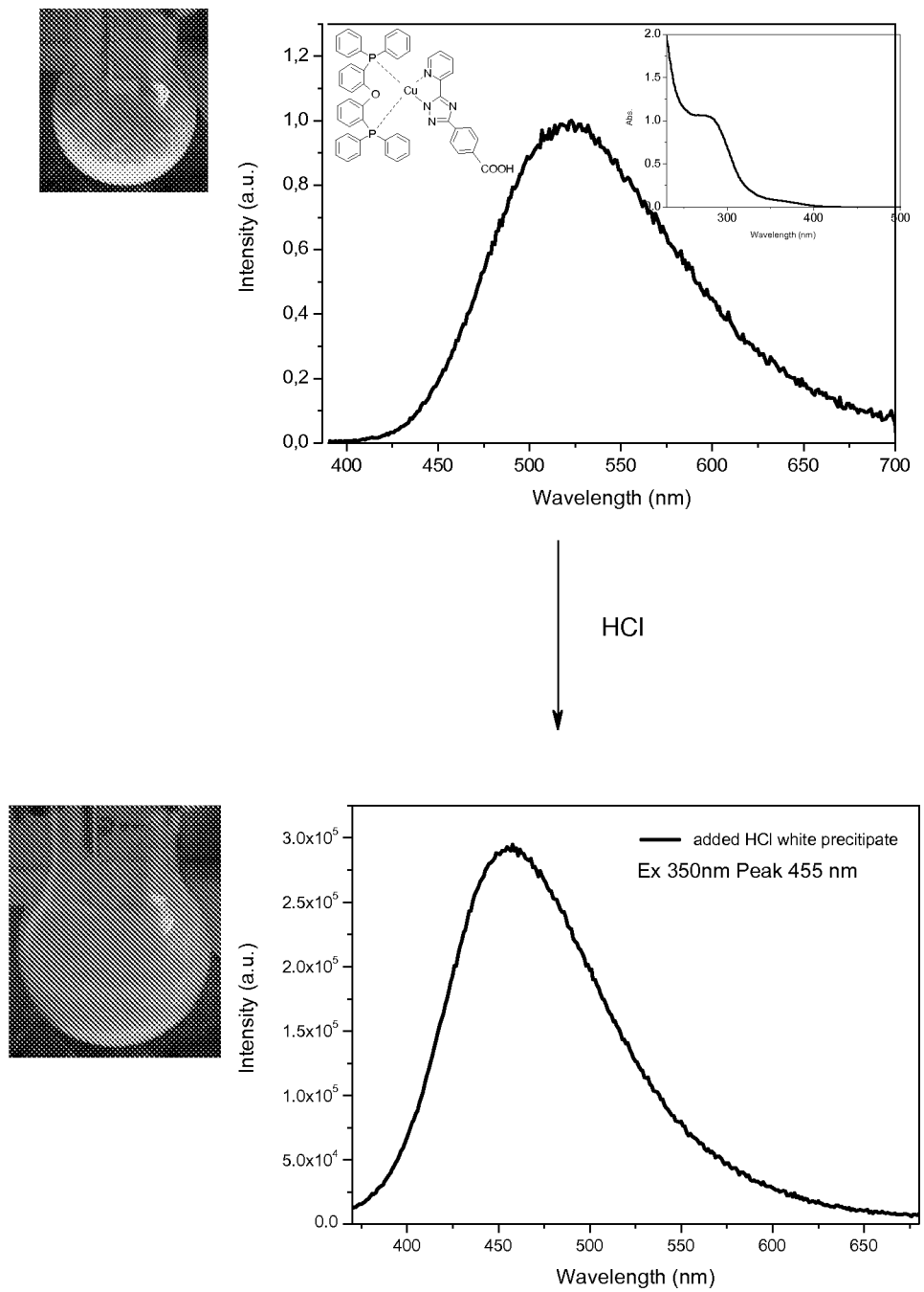
FIG. 8 shows emission shift of the compound of example 2 upon protonation.
Figure 9:
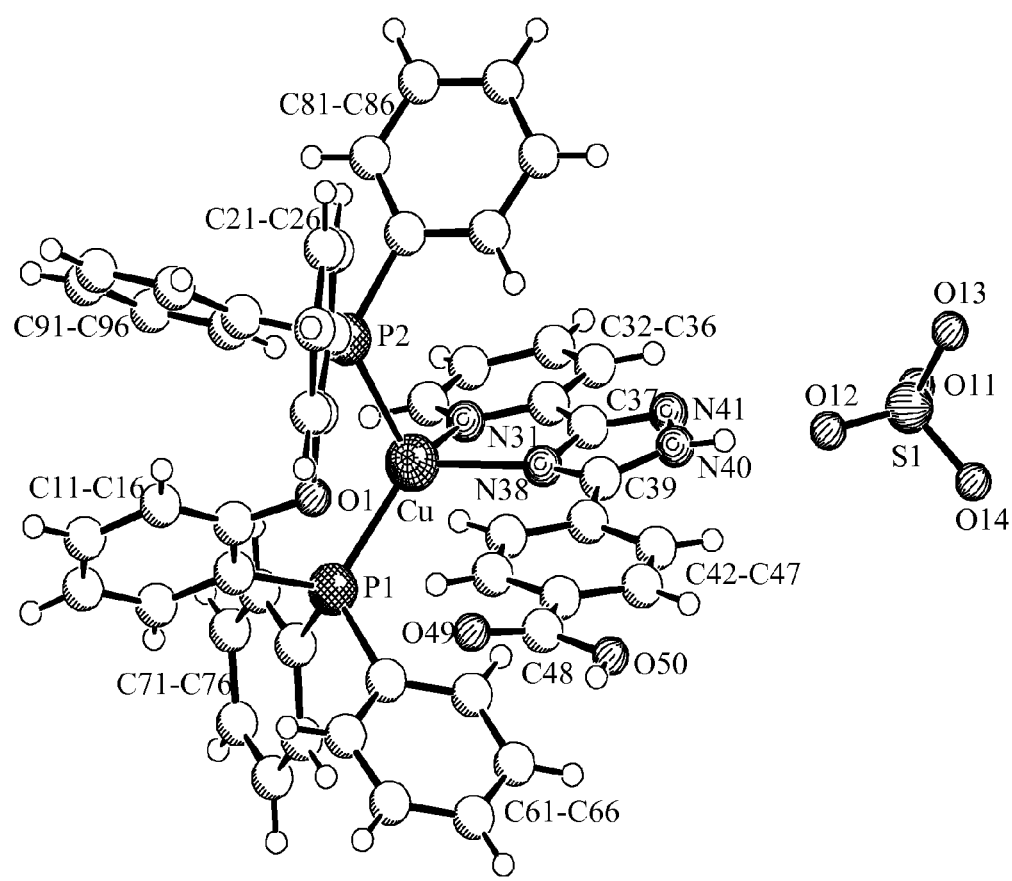
FIG. 9 shows the molecular structure of compound 2 (protonated form containing sulfate) as determined by x-ray diffractometry.
Figure 10:
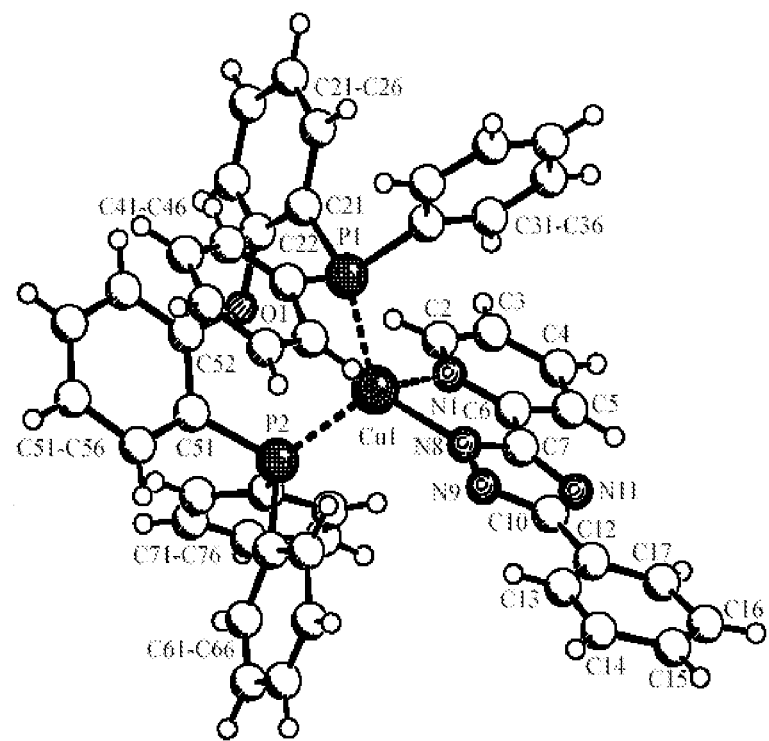
FIG. 10 shows the molecular structure of compound 1 as determined by x-ray diffractometry.
Figure 11:
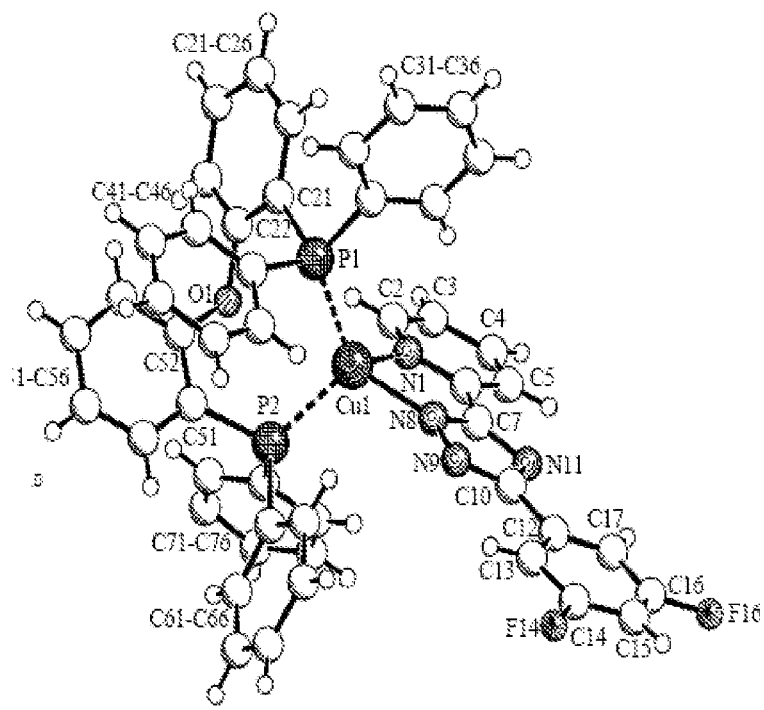
FIG. 11 shows the molecular structure of compound 5 as determined by x-ray diffractometry.
Figure 12:
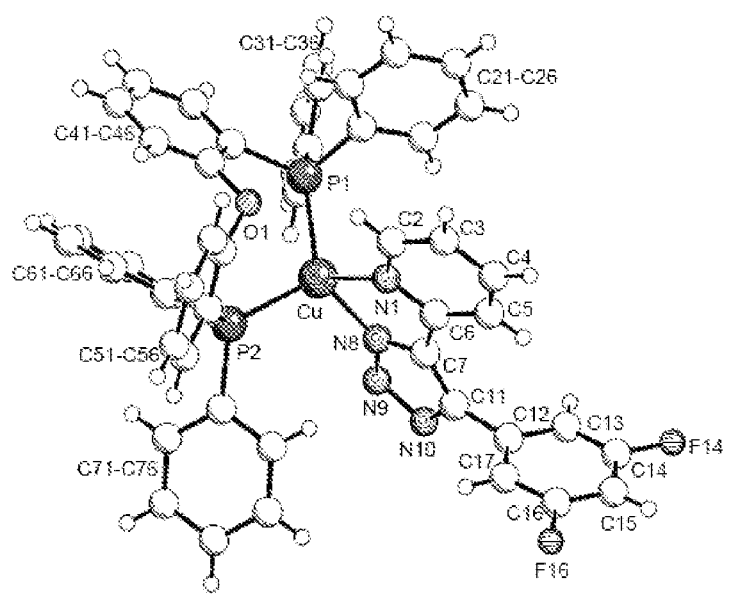
FIG. 12 shows the molecular structure of compound 13 as determined by x-ray diffractometry.

Spectral data (room temperature absorption spectra in DCM or THF, fluorescence emission of neat film on quartz, lifetimes of excited states) are compiled in the below table:

| COMPOUND NO. | absorption [a] $\lambda_{max}$, nm | Em [b], $\lambda_{max}$, nm | T [b] (µs) |
|---|---|---|---|
| 1 | 272 | 531 | 2.68 (15%) |
|   |     |     | 10.01 (85%) |
| 2 | 270 | 522 | 2.01 (34%) |
|   |     |     | 7.01 (66%) |
| 3 | 264 | 513 | 1.53 (21%) |
|   |     |     | 7.13 (79%) |
| 4 | 268 | 524 | 1.29 (20%) |
|   |     |     | 6.9 (80%) |
| 5 | 290 | 526 | 2.62 (17%) |
|   |     |     | 6.77 (83%) |
| 6 | 274 | 512 | 4.58 (25%) |
|   |     |     | 12.59 (75%) |
| 7 | 271 | 518 | 1.89 (19%) |
|   |     |     | 7.80 (81%) |
| 8 | 312 | 581 | 2.52 (33%) |
|   |     |     | 6.01 (67%) |
| 8 in PMMA |  | 534 | 4.2 (29%) |
|   |     |     | 15.3 (71%) |
| 10 | 288 | 445 | 14.01 (39%) |
|    |     |     | 2.86 (66%) |
| 12 | 286 | 506 | 5.07 (20%) |
|    |     |     | 11.58 (80%) |
| 13 |     | 512 | 3.43 (10%) |
|    |     |     | 11.1 (90%) |
| 14 |     | 531 | 2.29 (44%) |
|    |     |     | 6.60 (56%) |

[a] Absorption of Cu(I)complexes in THF solution,
[b] Emission and lifetime of Cu(I) complexes in neat films excited by 366 nm.

HOMO levels: Cyclic voltammetry (CV) is performed using a Voltalab® 40 system (Radiometer Analytical) which consists of a PGZ301 potentiostat and Voltamaster® 4 software. The working and the counter electrodes are a Pt-disc and a Pt wire respectively, whereas Ag wire is used as a pseudoreference electrode. All glasswares are dried prior to use. The dry electrolyte tetrabutyl ammonium hexafluorophosphate, (>99.0% purity), the analyte and ferrocene (FeCp2) used as the reference are dried and degassed at high temperature and at reduced pressure in a Schlenk flask in order to eliminate any moisture and oxygen. Results are compiled in the following table.

| COMPOUND NO. | HOMO (eV) |
|---|---|
| 1 | 5.46 |
| 2 | 5.54 |
| 4 | 5.44 |
| 5 | 5.45 |
| 3 | 5.47 |
| 6 | 5.72 |
| 13 | 5.58 |

Quantum Yield (QY) in Solid State:

Quantum yield of powder is measured using an appropriate apparatus from Hamamatsu C9920 and exciting the powder at 366 nm. Results are compiled in the following table.

| COMPOUND NO. | Ex. Wavelength | QY |
|---|---|---|
| 1 | 366 | 0.17 |
| 4 | 366 | 0.24 |
| 3 | 366 | 0.23 |
| 5 | 366 | 0.54 |
| 6 | 360 | 0.24 |
| 10 | 340 | 0.14 |
| 2 | 350 | 0.26 |
| 12 | 402 | 0.21 |
| 13 | 366 | 0.39 |

The crystal structure of the complexes are determined by standard x-ray diffraction procedures using single crystals.

The invention claimed is:

1. An electroneutral complex of the formula I

L Cu A    (I)

wherein
L stands for a bidentate neutral ligand which corresponds to the formula II

D$_1$-G-D$_2$    (II)

wherein G stands for a divalent organic bridging group selected from C$_1$-C$_8$alkylene, C$_2$-C$_8$alkenylene, C$_2$-C$_8$alkinylene O, S, SO, SO$_2$, O-interrupted C$_2$-C$_8$alkylene, phenylene, substituted phenylene, or a direct bond and D₁ and D₂, each independently, stand for an organic moiety containing an electron donating heteroatom selected from sulphur and/or phosphorus;

A stands for a bidentate monoanionic ligand binding to Cu— wherein the monoanionic ligand A is of the formulae (VI) or (VII)

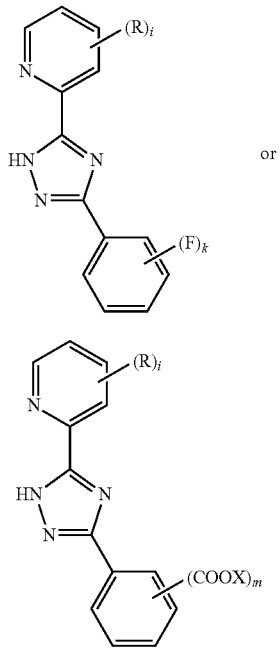

wherein i and m independently are 0, 1 or 2;

k is from the range 3-5;

R independently is $C_1$-$C_{12}$alkyl, $C_2$-$C_8$alkenyl, halogen, nitro, amino, methoxy;

X is H $C_1$-$C_{12}$alkyl or an equivalent of a cation such as Li+, Na+, K+, ½Ca2+, ½Mg2+, ½Zn2+.

2. The complex of claim 1, wherein the ligand L corresponds to the formula II

wherein G stands for a divalent organic bridging group selected from $C_1$-$C_8$alkylene, $C_2$-$C_8$alkenylene, $C_2$-$C_8$alkinylene, O, S, SO, SO₂, O-interrupted $C_2$-$C_6$alkylene, phenylene, substituted phenylene, or for a direct bond; and D₁, and D₂, each independently, are selected from phosphinyl moieties of the formula VI

D₅ and D₆ independently are $C_1$-$C_8$alkyl, $C_2$-$C_8$alkenyl, $C_2$-$C_8$alkinyl each of which is unsubstituted or substituted; and D₇ is $C_1$-$C_8$alkylene, $C_2$-$C_8$alkenylene, $C_2$-$C_8$alkinylene, each of which is unsubstituted or substituted.

3. The complex according to claim 1, wherein any substituent, if present, is selected from $C_1$-$C_{18}$alkoxy; $C_1$-$C_{18}$alkyl; said alkyl or alkoxy substituted by halogen, OH, COOH or CONH₂; said alkyl or alkoxy interrupted by O, S, COO or CONH; $C_2$-$C_8$alkenyl; $C_2$-$C_8$alkynyl; $C_4$-$C_{12}$cycloalkoxy; $C_4$-$C_{12}$cycloalkyl; OH; COOH; halogen; $C_1$-$C_{14}$aryl; said aryl substituted by $C_1$-$C_8$alkyl, $C_1$-$C_8$alkoxy, $C_1$-$C_8$haloalkyl, $C_2$-$C_8$alkenyl, $C_2$-$C_8$alkynyl, $C_1$-$C_8$alkoxycarbonyl, $C_1$-$C_8$alkanoyloxy, nitro, halogen, OH, COOH, CONH₂; where saturated carbons also may be substituted by oxo (=O), adjacent substituents may be linked together to form a carbocyclic, lactone, anhydride, cyclic ether ring.

4. An organic electronic device, I, comprising an emitting layer wherein the emitting layer comprises a compound according to claim 1.

5. The device of claim 4, further comprising a hole transport material, selected from polyvinyl-carbazol, N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde-diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5[p-(diethylamino)phenyl]pyrazoline (PPR or DEASP), 1,2-trans-bis(9H-carbazol-9-yl)cyclobutane (DCZB), N,N,N',N'-tetrakis (4-methylphenyl)-(1,1-biphenyl)-4,4'-diamine (TTB), 4,4'-N,N-dicarbazole-biphenyl (CBP), N,N-dicarbazoyl-1,4-dimethene-benzene(DCB), porphyrinic compounds, (phenylmethyl) polysilane, poly(3, 4-ethylendioxythiophene) (PEDOT), polyaniline, and combinations thereof, or one or more of the above components doped into a polymer selected from the group consisting of polystyrene and polycarbonate.

6. A method for the preparation of a light emitting device, which method comprises providing an organic substance layer containing a complex or complex salt according to claim 1 between a pair of electrodes on a substrate.

7. A device selected from stationary and mobile displays, selected from the group consisting of displays for computers, mobile phones, laptops, pdas, TV sets, displays in printers, kitchen equipment, billboards, lightings, information boards and destination boards for trains and buses, containing an emitting layer according to claim 4.

* * * * *